US011397179B2

(12) United States Patent
Shin et al.

(10) Patent No.: US 11,397,179 B2
(45) Date of Patent: Jul. 26, 2022

(54) PH-MODULATED IMAGING OF TARGETS CLOSE TO A SOLID SURFACE

(71) Applicant: Robert Bosch GmbH, Stuttgart (DE)

(72) Inventors: Young Shik Shin, Mountain View, CA (US); Patrick A. Staley, Sunnyvale, CA (US); Nadia Fomina, Sunnyvale, CA (US); Christopher Johnson, San Carlos, CA (US)

(73) Assignee: Robert Bosch GmbH, Stuttgart (DE)

( * ) Notice: Subject to any disclaimer, the term of this patent is extended or adjusted under 35 U.S.C. 154(b) by 268 days.

(21) Appl. No.: 16/355,113

(22) Filed: Mar. 15, 2019

(65) Prior Publication Data

US 2020/0209225 A1    Jul. 2, 2020

Related U.S. Application Data

(60) Provisional application No. 62/787,162, filed on Dec. 31, 2018.

(51) Int. Cl.
| | | |
|---|---|---|
| *G01N 33/52* | (2006.01) | |
| *G01N 27/30* | (2006.01) | |
| *G01N 21/76* | (2006.01) | |
| *G01N 21/64* | (2006.01) | |
| *G01N 21/17* | (2006.01) | |

(52) U.S. Cl.
CPC ......... *G01N 33/52* (2013.01); *G01N 21/1717* (2013.01); *G01N 21/6428* (2013.01); *G01N 21/6458* (2013.01); *G01N 21/76* (2013.01); *G01N 27/302* (2013.01); *G01N 2021/6439* (2013.01)

(58) Field of Classification Search
CPC ...... G01N 33/52; G01N 27/302; G01N 21/76; G01N 21/6428; G01N 2021/6439; G01N 21/6458; G01N 33/84; G01N 21/1717
See application file for complete search history.

(56) References Cited

U.S. PATENT DOCUMENTS

| | | |
|---|---|---|
| 8,105,471 B1 | 1/2012 | Han et al. |
| 8,383,337 B2 | 2/2013 | Lu et al. |
| 8,758,576 B2 | 6/2014 | Escoffier et al. |
| 9,188,585 B2 | 11/2015 | Kavusi et al. |

(Continued)

FOREIGN PATENT DOCUMENTS

| | | | | |
|---|---|---|---|---|
| CN | 106501228 A | * | 3/2017 | ......... G01N 21/6456 |
| GB | 2266182 A | * | 10/1993 | ......... H01L 51/5012 |

(Continued)

OTHER PUBLICATIONS

Liu, et al., "Physiological monitoring of optically trapped cells: assessing the effects of confinement by 1064-nm laser tweezers using microfluorometry", Oct. 1996, Biophysical Journal, vol. 71 (4), pp. 2158-2167 (Year: 1996).*

(Continued)

*Primary Examiner* — Samuel P Siefke
*Assistant Examiner* — Henry H Nguyen
(74) *Attorney, Agent, or Firm* — Michael Best & Friedrich LLP

(57) ABSTRACT

Provided are methods for imaging a biospecimen, which involves the use of electrochemical pH modulation in combination with pH-sensitive labels to achieve localized imaging with a high vertical axial resolution.

20 Claims, 5 Drawing Sheets

(56) References Cited

U.S. PATENT DOCUMENTS

| | | |
|---|---|---|
| 9,567,678 B2 | 2/2017 | Eltayeb et al. |
| 9,677,125 B2 | 6/2017 | Sood et al. |
| 9,766,197 B2 | 9/2017 | Johnson et al. |
| 9,810,688 B2 | 11/2017 | Fomina et al. |
| 9,874,538 B2 | 1/2018 | Johnson et al. |
| 9,877,770 B2 | 1/2018 | Wong et al. |
| 9,903,820 B2 | 2/2018 | Meller et al. |
| 9,910,008 B2 | 3/2018 | Johnson et al. |
| 10,011,549 B2 | 7/2018 | Johnson et al. |
| 10,041,905 B2 | 8/2018 | Johnson et al. |
| 10,101,315 B2 | 10/2018 | Meller et al. |
| 2003/0059820 A1 | 3/2003 | Vo-Dinh |
| 2012/0115236 A1 | 5/2012 | Chen et al. |
| 2016/0003766 A1 | 1/2016 | Johnson et al. |
| 2017/0010238 A1 | 1/2017 | Johnson et al. |
| 2018/0318834 A1 | 11/2018 | Fomina et al. |

FOREIGN PATENT DOCUMENTS

| | | |
|---|---|---|
| WO | 2003043402 A2 | 5/2003 |
| WO | 2017/005587 A1 | 1/2017 |
| WO | 2018178992 A1 | 10/2018 |

OTHER PUBLICATIONS

Translation of CN106501228A, Zeng, Shao-qun, Mar. 15, 2017 (Year: 2017).*

International Search Report and Written Opinion for Application No. PCT/IB2019/001438 dated May 13, 2020 (17 pages).

Zhang et al., "Hierarchical Nanowire Arrays as Three-Dimensional Fractal Nanobiointerfaces for High Efficient Capture of Cancer Cells", Nano Letters, vol. 16, 2016, pp. 766-772.

Wen-feng Gou, Dao-fu Shen, Xue-feng Yang, Shuang Zhao, Yun-peng Liu, Hong-zhi Sun, Rong-jian Su, Jun-sheng Luo, and Hua-chuan Zheng. "ING5 suppresses proliferation, apoptosis, migration and invasion, and induces autophagy and differentiation of gastric cancer cells: a good marker for carcinogenesis and subsequent progression". Oncotarget (2015) vol. 6, iss. 23, pp. 19552-19579.

Parthasarathy Arumugam, Annie Samson, Jieun Ki, and Joon Myong Song. "Knockdown of clusterin alters mitochondrial dynamics, facilitates necrosis in camptothecin-induced cancer stem cells". Cell Biology and Toxicology (2017) vol. 33, iss. 3, pp. 307-321.

Hyunbum Jang, Sherwin J. Abraham, Tanmay S. Chavan, Ben Hitchinson, Lyuba Khavrutskii, Nadya I. Tarasova, Ruth Nussinov, and Vadim Gaponenko "Mechanisms of Membrane Binding of Small GTPase K-Ras4B Farnesylated Hypervariable Region". The Journal of Biological Chemistry (2015), vol. 290, No. 15, pp. 9465-9477.

Guan-Yu Chen, Zeyang Li, Joao N. Duarte, Alexandre Esteban, Ross W. Cheloha, Christopher S. Theile, Gerald R. Fink, Hidde L. Ploegh. "Rapid capture and labeling of cells on single domain antibodies-functionalized flow cell". Biosensors and Bioelectronics (2017) vol. 89, part 2, pp. 789-794.

Zhaobo He, Feng Guo, Chun Feng, Bo Cai, James P. Lata, Rongxiang He, Qinqin Juang, Xiaolei Yu, Lang Rao, Huiqin Liu, Shishang Guo, Wei Liu, yuanzhen Zhang, Tony Jun Huang, and Xingzhong Zhao. "Fetal nucleated red blood cell analysis for non-invasive prenatal diagnostics using a nanostructure microchip". Journal of Materials Chemistry B (2017) vol. 5, pp. 226-235.

N. Fomina, C. A. Johnson, A. Maruniak, S. Bahrampour, C. Lang, R. W. Davis, S. Kavusi, and H. Ahmad, "An electrochemical platform for localized pH control on demand," Lab Chip (2016) 16, pp. 2236-2244.

V. Vojinovic', A.M. Azevedo, V.C.B. Martins, J.M.S. Cabral,T.D. Gibson, L.P. Fonseca, "Assay of H2O2 by HRP catalysed co-oxidation of phenol-4-sulphonic acid and 4-aminoantipyrine: characterisation and optimisation," Journal of Molecular Catalysis B: Enzymatic (2004), 28, pp. 129-135.

Maurer K, Cooper J, Caraballo M, et al., "Electrochemically Generated Acid and Its Containment to 100 Micron Reaction Areas for the Production of DNA Microarrays," PLoS One (2006), 1(1):e34.

Julie Doucet, An Zhao, Jean Fu, and Alexandre Avrameas, "Development and Validation of an ELISA at Acidic pH for the Quantitative Determination of IL-13 in Human Plasma and Serum," Disease Markers (2013), 35:5, pp. 465-474.

Stephan Fellner, Simone Hentze, Uwe Kempin, Evelyn Richter, Jorg Rocktaschel, and Barbara Langer. "Analytical evaluation of a BNP assay on the new point-of-care platform responsS IQ". Practical Laboratory Medicine (2015) vol. 2, pp. 15-21.

International Preliminary Report on Patentability for Application No. PCT/IB2019/001438 dated Jun. 16, 2021 (9 pages).

* cited by examiner

PH-MODULATED IMAGING OF TARGETS CLOSE TO A SOLID SURFACE

CROSS-REFERENCE TO RELATED APPLICATION

This application claims the benefit of and priority to U.S. Provisional Application No. 62/787,162, filed on Dec. 31, 2018, the content of which is incorporated by reference herein in its entirety, and priority to which is hereby claimed.

FIELD

The present disclosure relates to an imaging method for a biospecimen, which involves electrochemical pH modulation and pH-sensitive labels.

BACKGROUND

Studying specific biological processes, such as cell-membrane related phenomena and vesicle-based transport, may be facilitated by collecting images from a very thin, well-defined layer of the sample. Currently available methods that may accomplish this include confocal microscopy, total internal reflectance fluorescence (TIRF) microscopy, and surface plasmon resonance enhanced fluorescent (SPRF) imaging. Confocal microscopy uses a pinhole aperture to focus on only a very thin layer of the target sample. TIRF activates only the dyes near the surface by internally reflecting the laser light so that the evanescent field only extends a short distance into the solution. SPRF is based on surface plasmon evanescent waves to excite the fluorophores locating at the interface. Atomic force microscopy (AFM) also provides topographic information on a small, localized surface region. Scanning electrochemical microscopy (SECM) is often used to probe local electrochemical interface behavior in addition to the topographic information.

Common biological applications of these imaging techniques include observing apoptosis and necrosis of cells, binding of various substrates to the surfaces of cells, and binding of various ligands to capture agents such as proteins, DNAs, RNAs, aptamers, peptides, polysaccharides, or other biomolecules. These applications require high vertical resolution to effectively capture the information from the well-defined localized region of interest. As a result, currently available solutions (e.g., the imaging technologies mentioned above) require special sets of optical and/or physical components, which typically are supplied as expensive standalone systems or high-cost add-on equipment.

SUMMARY

Therefore, there remains a need for inexpensive solutions that provide a localized imaging that is compatible with existing microscopic instruments and may be used in a broad range of biological applications.

In one aspect, the present disclosure provides a method for imaging a biospecimen, comprising
(a) labeling the biospecimen with a pH-sensitive label to form a labeled biospecimen,
(b) submerging the labeled biospecimen and a surface of an electrode in a buffered solution having a pH value, wherein
the buffered solution comprises a pH modulating agent;
the surface optionally comprises microstructures;
the labeled biospecimen is coupled to the surface or to the microstructures; and
the microstructures, when present, define a volume between the biospecimen and
the surface, through which the pH modulating agent diffuses,
(c) applying a potential or a current to the electrode, whereupon the pH modulating agent causes a change in the pH value in a zone adjacent to the surface of the electrode, thereby causing the pH-sensitive label within the zone to produce an optical signal, and
(d) detecting the optical signal thereby imaging the labeled biospecimen.

In another aspect, the present disclosure provides method for imaging a biospecimen, comprising
(a) labeling the biospecimen with a pH-sensitive label to form a labeled biospecimen,
(b) submerging the labeled biospecimen and a surface of an electrode in a buffered solution having a pH value, wherein
the surface comprises a coating;
the coating comprises a pH modulating agent;
the coating optionally comprises microstructures;
the buffered solution optionally comprises the pH modulating agent;
the labeled biospecimen is coupled to the coating or to the microstructures; and
the microstructures, when present, define a volume between the biospecimen and the surface, through which the pH modulating agent in the buffered solution, when present, diffuses,
(c) applying a potential or a current to the electrode, whereupon the pH modulating agent causes a change in the pH value in a zone adjacent to the coating, thereby causing the pH-sensitive label within the zone to produce an optical signal, and
(d) detecting the optical signal thereby imaging the labeled biospecimen Other aspects, features, and embodiments will become apparent by consideration of the detailed description and accompanying drawings.

DETAILED DESCRIPTION

Figure 1A:
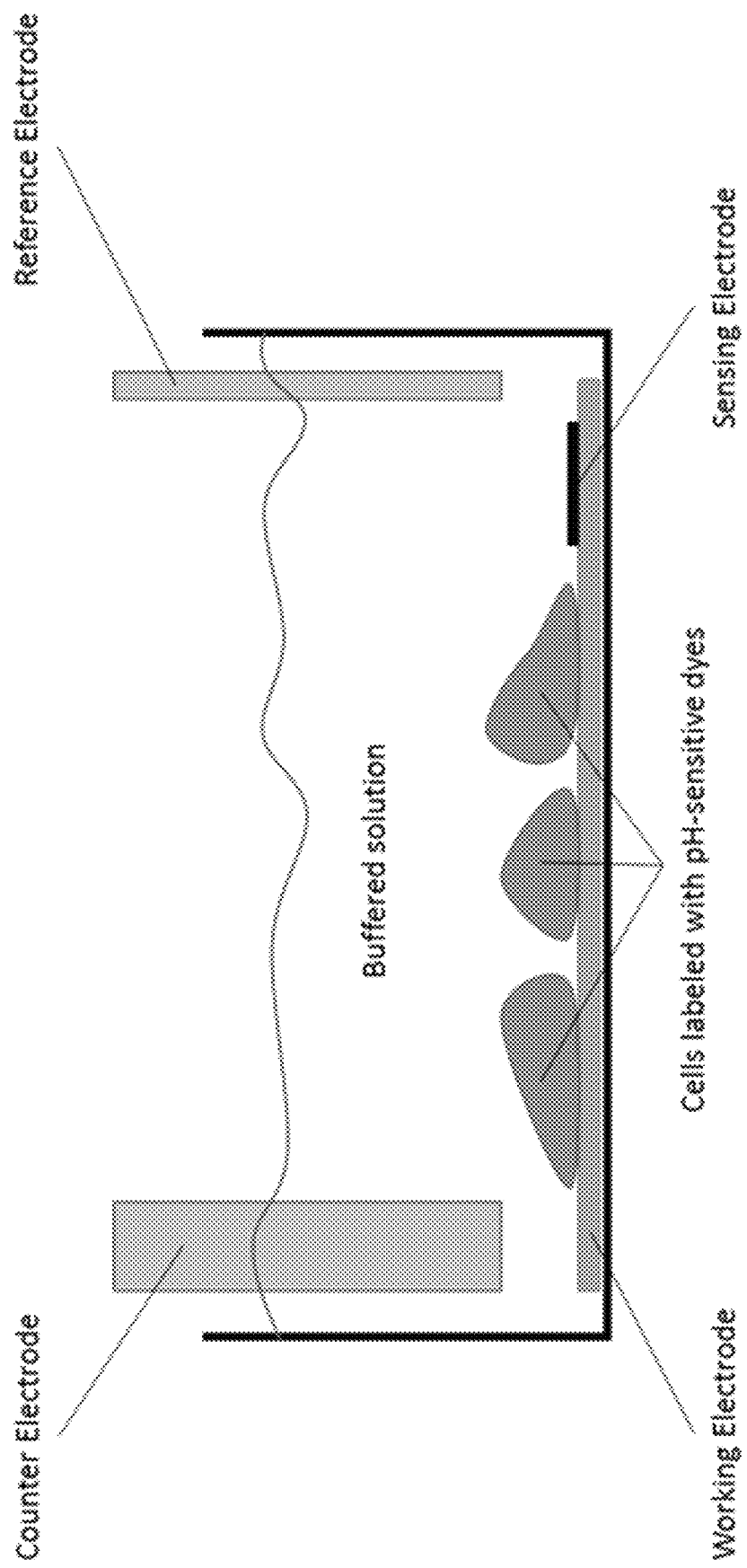
FIG. 1A is a schematic illustrating a system for pH-modulated imaging, in which pH modification is not in effect.

Before any embodiments are explained in detail, it is to be understood that this disclosure is not intended to be limited in its application to the details of construction and the arrangement of components set forth in the following description or illustrated in the following drawings. Embodiments are capable of other configurations and of being practiced or of being carried out in various ways.

The present disclosure provides a technical solution to perform imaging of a biospecimen with a very small imaging window close to a surface that can be added to existing imaging platforms, such as fluorescent microscopes. The present technology involves the use of electrochemical pH modulation to achieve localized imaging of a biospecimen labeled with a pH-sensitive label. The present technology may achieve a high vertical axial resolution, similar to confocal microscopy or total internal reflectance fluorescence (TIRF) microscopy.

The terms "comprise(s)," "comprising," "include(s)," "including," "having," "has," "contain(s)," "containing," and variants thereof, as used herein, are open-ended transitional phrases, terms, or words that are meant to encompass the items listed thereafter and equivalents thereof as well as additional items. The singular forms "a", "and", and "the" include plural references unless the context clearly dictates otherwise. Where the term "comprising" is used, the present disclosure also contemplates other embodiments "comprising", "consisting of", and "consisting essentially of", the embodiments or elements presented herein, whether explicitly set forth or not.

Any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March March's Advanced Organic Chemistry, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

In one aspect, the present disclosure provides methods for imaging a biospecimen, comprising
  (a) labeling the biospecimen with a pH-sensitive label to form a labeled biospecimen,
  (b) submerging the labeled biospecimen and a surface of an electrode in a buffered solution having a pH value, wherein
    the buffered solution comprises a pH modulating agent;
    the surface optionally comprises microstructures;
    the labeled biospecimen is coupled to the surface or to the microstructures; and
    the microstructures, when present, define a volume between the biospecimen and the surface, through which the pH modulating agent diffuses,
  (c) applying a potential or a current to the electrode, whereupon the pH modulating agent causes a change in the pH value in a zone adjacent to the surface of the electrode, thereby causing the pH-sensitive label within the zone to produce an optical signal, and
  (d) detecting the optical signal thereby imaging the labeled biospecimen.

In another aspect, the present disclosure provides methods for imaging a biospecimen, comprising
  (a) labeling the biospecimen with a pH-sensitive label to form a labeled biospecimen,
  (b) submerging the labeled biospecimen and a surface of an electrode in a buffered solution having a pH value, wherein
    the surface comprises a coating;
    the coating comprises a pH modulating agent;
    the coating optionally comprises microstructures;
    the buffered solution optionally comprises the pH modulating agent;
    the labeled biospecimen is coupled to the coating or to the microstructures; and
    the microstructures, when present, define a volume between the biospecimen and the surface, through which the pH modulating agent in the buffered solution, when present, diffuses,
  (c) applying a potential or a current to the electrode, whereupon the pH modulating agent causes a change in the pH value in a zone adjacent to the coating, thereby causing the pH-sensitive label within the zone to produce an optical signal, and
  (d) detecting the optical signal thereby imaging the labeled biospecimen.

The biospecimen may be coupled to the surface, or coating, or microstructures as described herein through various physical or chemical interactions between the biospecimen and the corresponding part on the surface, coating, or microstructures. Examples of such interactions include, but not limited to, contacting, adherence, covalent bonding, hydrogen bonding, ionic bonding, ligand-receptor binding, and antigen-antibody binding. In some embodiments, the coupling may be in the form of simple contacting or adherence. For example, the biospecimen may be placed in physical contact with, or adhere to, the surface, coating, or microstructures in the present methods. The biospecimen may have at least one part of its structure coupled to at least one corresponding part on the surface, coating, or microstructures.

The biospecimen may be a fixed tissue, cells such as fixed cells and live cells, extracellular vesicles, and surface patterned biomolecules such as proteins, DNAs, RNAs, and peptides, or combinations thereof. In some embodiments, the biospecimen is a tissue sample, a cell, a small vesicle, or a combination thereof. In some embodiments, the biospecimen is a cell.

The pH-sensitive label disclosed herein refers to any agent that produces an optical signal, directly or indirectly, in response to a change of pH value. Suitable pH-sensitive labels include, but are not limited to, a fluorescent dye, a fluorescent protein, an enzyme, and combinations thereof. The biospecimen may be labeled by the pH-sensitive label using methods known in the art. In some embodiments, the labeling methods may include the use of known labeled capture agents such as antibodies, DNA, RNA, aptamers, peptides, lipids, and small molecules. In some embodiments, the labeling methods may include chemical modification through a functional group, such as methoxy- or ethoxy-, acetoxy-, and trichlorosilane, primary or secondary amine, NHS ester, maleimide, azides, or thiol.

In some embodiments, the pH-sensitive label is a pH-sensitive fluorescent dye. Suitable fluorescent dyes include, but are not limited to pHrodo, Protonex, Oregon Green, LysoSensor Green, pHAb, fluorescein, FAM, rhodamine B derivatives, and SNARF.

Suitable fluorescent proteins include, but are not limited to green fluorescent protein, yellow fluorescent protein, and cyan fluorescent protein. In some embodiments, the fluorescent protein is green fluorescent protein (GFP).

Suitable enzymes useful as pH-sensitive labels include, but are not limited to, horseradish peroxidase (HRP), glucose oxidase, and alkaline phosphatase.

The pH modulating agent refers to a compound or a composition that undergoes a chemical reaction in a solution in response to electrical potentials or currents thereby causing a change in the pH value of the solution. The chemical reaction may be a redox reaction, in which the redox state of the pH modulating agent is changed. Electrochemical oxidation and/or reduction of the pH modulating agents via electrical stimulus may introduce local pH change through the equilibration between generation or consumption of protons and buffering capacity of the buffer solution. This may generate a pH modulation zone with a very short vertical distance, for example from several nm to several μm, from the surface of the electrode, which allows imaging of biospecimen only within the pH modulation volume. In some embodiments, the pH modulating agents may include materials that can perform proton coupled electron transfer. Suitable pH modulating agents include, but are not limited to quinone derivatives, aminophenol derivatives, aniline derivatives, benzidine derivatives, hydrazine derivatives, phenol-Ru(2,2'-bipyridine)$_3^{2+}$, and combinations thereof. Suitable pH modulating agents may also include other known compounds having pH-responding moieties not exemplified above.

In some embodiments, the pH modulating agent is a quinone derivative of any of formula (I)-(XII)

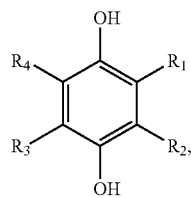

(I)

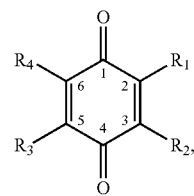

(II)

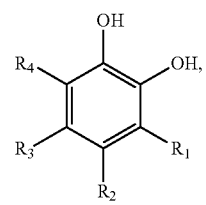

(III)

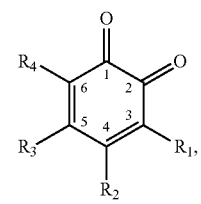

(IV)

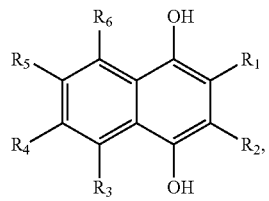

(V)

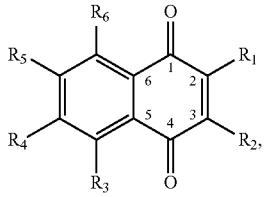

(VI)

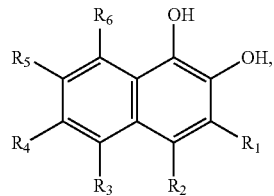

(VII)

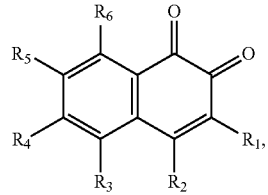

(VIII)

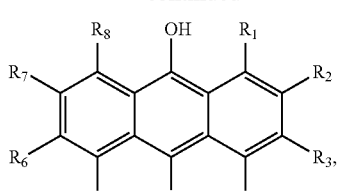

(IX)

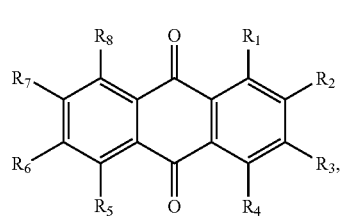

(X)

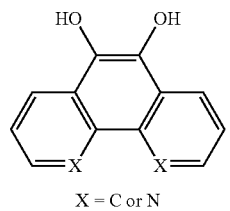

X = C or N (XI)

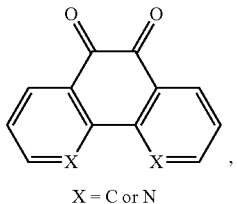

X = C or N (XII)

wherein $R_1$, $R_2$, $R_3$, $R_4$, $R_5$, $R_6$, $R_7$, and $R_8$ are each independently selected from the group consisting of: H; $C_nH_{2n+1}$; Cl; F; I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_y$ COOH; $O(C_nH_{2n}O)_yCOOM$; COOH; COOM; $COOC_nH_{2n+1}$; $CONHC_nH_{2n+1}$; $CON(C_nH_{2n+1})_2$; $SO_3H$; $SO_3M$; $NH_2$; $NHC_nH_{2n+1}$; $N(C_nH_{2n+1})_2$; $NHC_nH_{2n}OH$; $NHC_nH_{2n}NH_2$; $N(C_nH_{2n}OH)_2$; $N(C_nH_{2n}NH)_2$; $NHCOC_nH_{2n+1}$; $NC_nH_{2n}COC_nH_{2n+1}$; $NC_nH_{2n}COC_nH_{2n}OH$; $NC_nH_{2n}COC_nH_{2n}NH_2$; $NC_nH_{2n}COC_nH_{2n}SH$; SH; $SC_nH_{2n+1}$; $SC_nH_{2n}OH$; $S(C_nH_{2n}O)_yOH$; $S(C_nH_{2n}O)_yOC_nH_{2n+1}$; $S(C_nH_{2n}O)_y$ COOH; $S(C_nH_{2n}O)_yCOOM$; $OC_nH_{2n}SH$; $O(C_nH_{2n}O)_ySH$; $O(C_nH_{2n}O)_ySC_nH_{2n+1}$; $C_nH_{2n}$; $C_nH_{2n}OC_nH_{2n}$; $C_nH_{2n}SC_nH_{2n}$; $C_nH_{2n}NHC_nH_{2n}$; $C_nH_{2n}N(C_nH_{2n+1})C_nH_{2n}$; $C_nH_{2n+1}$; $C_nH_{2n}OH$; $C_nH_{2n+1}OC_nH_{2n}$; $C_nH_{2n}OC_nH_{2n}OH$; $C_nH_{2n}O(C_nH_{2n}O)_yCOOH$; $C_nH_{2n}O(C_nH_{2n}O)_yCOOM$; $C_nH_{2n}COOH$; $C_nH_{2n}COOM$; $C_nH_{2n}COOC_nH_{2n+1}$; $C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$; $C_nH_{2n}NHC_nH_{2n+1}$; $C_nH_{2n}N(C_nH_{2n+1})_2$; $C_nH_{2n}NHC_nH_{2n}OH$; $C_nH_{2n}NHC_nH_{2n}NH_2$; $C_nH_{2n}N(C_nH_{2n}OH)_2$; $C_nH_{2n}N(C_nH_{2n}NH_2)_2$; $C_nH_{2n}NHCOC_nH_{2n+1}$; $C_nH_{2n}NC_nH_{2n}COC_nH_{2n}OH$; $C_nH_{2n}NC_nH_{2n}COC_nH_{2n}NH_2$; $C_nH_{2n}NC_nH_{2n}COC_nH_{2n}SH$; $C_nH_{2n}SH$; $C_nH_{2n+1}SC_nH_{2n}$; $C_nH_{2n}SC_nH_{2n}OH$; $C_nH_{2n}S(C_nH_{2n}O)_yOH$; $C_nH_{2n}S(C_nH_{2n}O)_yOC_nH_{2n+1}$; $C_nH_{2n}S(C_nH_{2n}O)_yCOOH$; $C_nH_{2n}S(C_nH_{2n}O)_yCOOM$; sugars; peptides; and amino acids, wherein M is any metal cation or $NH_4^+$, n is an integer from 1 to $10^9$, and y is an integer from 1 to $10^9$.

In some embodiments, $R_1$, $R_2$, $R_3$, $R_4$, $R_5$, $R_6$, $R_7$, and $R_8$ are each independently selected from the group consisting of: $C_nH_{2n}OH$; $C_nH_{2n}OC_nH_{2n}OH$; $C_nH_{2n}O(C_nH_{2n}O)_yCOOH$; $C_nH_{2n}O(C_nH_{2n}O)_yCOOM$; $C_nH_{2n}COOH$; $C_nH_{2n}COOM$; $C_nH_{2n}COOM$; $C_nH_{2n}COOC_nH_{2n+1}$; $C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$; $C_nH_{2n}NHC_nH_{2n+1}$; $C_nH_{2n}N(C_nH_{2n+1})_2$; $C_nH_{2n}NHC_nH_{2n}OH$; $C_nH_{2n}NHC_nH_{2n}NH_2$; $C_nH_{2n}N(C_nH_{2n}OH)_2$; $C_nH_{2n}N(C_nH_{2n}NH_2)_2$; $C_nH_{2n}NHCOC_nH_{2n+1}$; $C_nH_{2n}NC_nH_{2n}COC_nH_{2n}OH$; $C_nH_{2n}NC_nH_{2n}COC_nH_{2n}NH_2$; $C_nH_{2n}NC_nH_{2n}COC_nH_{2n}SH$; $C_nH_{2n}SH$; $C_nH_{2n}SC_nH_{2n}OH$; $C_nH_{2n}S(C_nH_{2n}O)_yOH$; $C_nH_{2n}S(C_nH_{2n}O)_yOC_nH_{2n+1}$; $C_nH_{2n}S(C_nH_{2n}O)_yCOOH$; and $C_nH_{2n}S(C_nH_{2n}O)_yCOOM$.

Suitable quinone derivatives may contain various functional groups to tune their solubility, biocompatibility, and electrochemical properties. Other examples of suitable quinone derivatives include those described in U.S. Pat. Nos. 9,766,197, 9,874,538, 9,910,008, 10,011,549, 10,041,905, US20170010238, and WO2017005587 (PCT/EP2016/065252), the entire contents of which are incorporated herein by reference.

The buffered solution refers to an aqueous or organic solution that may maintain its pH value at a nearly constant level and does not interfere with the operation of the imaging instruments. In some embodiments, the buffered solution is an aqueous solution, such as phosphate buffer, citrate buffer, acetate buffer, or other buffers used in biological applications. In some embodiments, the buffered solution is a solution in which the biological functions of the biospecimen may be detected or monitored. For example, the buffered solution may be a medium for cell culture.

In some embodiments, the biospecimen labeled with a pH-sensitive label is coupled to (e.g., in contact with) the surface of the electrode directly. In some embodiments, the electrode comprises a coating on its surface and the biospecimen is coupled to (e.g., in contact with) the coating. The coating may form a layer that covers a part of the electrode surface or the entire electrode surface. In some embodiments, the biospecimen and the surface of electrode to which the biospecimen is coupled are submerged in the buffered solution. In some embodiments, the biospecimen and the coating on the electrode surface to which the biospecimen is coupled are submerged in the buffered solution.

In some embodiments, the buffered solution comprises a pH modulating agent as disclosed herein. For example, the pH modulating agent may be homogenously dissolved in the buffered solution.

In some embodiments, the coating on the electrode surface includes a pH modulating agent. For example, the pH modulating agent may be embedded or immobilized in the coating layer. The pH modulating agent embedded layer may be a monolayer of small molecules, or a polymer layer, or a 3-D cross-linked metal/polymer composite network. The layer may be covalently attached, or physically adsorbed to the electrode. In some embodiments, the electrode or the pH modulating agent embedded layer may be optically transparent. In some embodiments, a conductive polymer may be used as both the electrode and pH modulating agent layer. Conductive polymers may be, for example, polypyrrole, polythiophene, polyfluorene, or polyaniline, etc.

In certain embodiments, the pH modulating agent may be covalently attached to the surface of the electrode through a functional group, such as methoxy- or ethoxy-, acetoxy-, and trichlorosilane, primary or secondary amine, NHS ester, maleimide, azides, or thiol. In certain embodiments, the coating on the electrode surface comprises a polymer and the pH modulating agent is integrated in the polymer as a part of a backbone of the polymer or as a side chain of the polymer.

As non-limiting examples, pH modulating agents that may be embedded in the coating layer are shown in Scheme 1. The pH modulating agents may be functionalized for a redox reaction to generate acid ($H_3O^+$), or base ($OH^-$). Scheme 1 panel (a) illustrates a monolayer of small molecules functionalized with phosphate groups, which may bind to a glass electrode. Scheme 1 panel (b) illustrates conductive polymer for electrode or electrode functionalized with quinone as a pendant group, resulting in a polymer with controllable film thickness. Scheme 1 panel (c) illustrates polymers that are functionalized with hydrophilic groups, which may be optionally mixed with the polymers that are for the functionalization with pH modulating agents in order to increase water, hydroxide, and hydronium permeation into the polymer, or co-polymerized with pH modulating agents. For example, hydrophilic polymers may be incorporated with the pH modulating agents in order to increase water permeation into the polymer layer. The pH modulation functionality and hydrophilic groups may be combined in the same polymer (co-polymerized). Alternatively, two polymers, one containing pH modulation functionality and other containing hydrophobic moieties, may be physically mixed together.

In some embodiments, both the buffered solution and the coating on the electrode surface includes a pH modulating agent.

In Scheme 1 panels (a) and (b), the oxidized forms of the pH modulating agents are shown on the left and the reduced forms are shown on the right, and pH modulation may be accomplished via release or uptake of protons by the electrochemically active moieties in the pH modulating agent embedded layer. For example, to make the layer of solution near the electrode more acidic compared to the bulk solution, the pH modulating agents in the layer are converted from the reduced form to the oxidized form; to make the pH of the layer of the solution near the electrode more basic, the pH modulating agents in the layer are converted from the oxidized state to the reduced state. In both of these cases, a quinone/hydroquinone moiety is used as a non-limiting example of the pH modulation-capable functional group. Other suitable pH modulating agents having similar functional groups may also be used.

The optical signal produced in the present method may be a colorimetric signal such as change of color, a chemiluminescent signal such as chemiluminescence emission, or a fluorescent signal such as fluorescence emission. The production and strength of the optical signal depends on the pH-sensitive labels on the biospecimen. In some embodi-

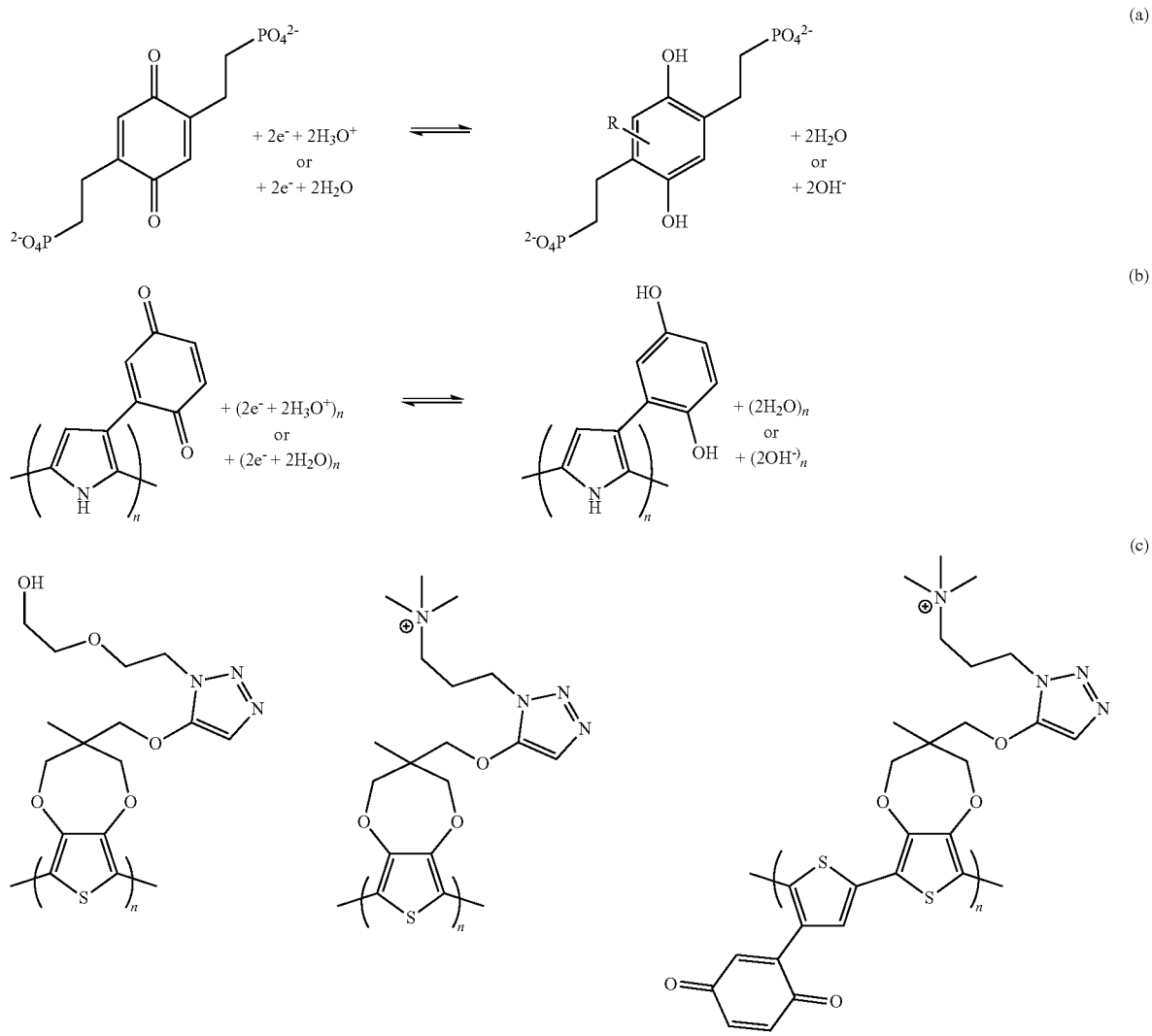

ments, the optical signal is fluorescence emission from the pH-sensitive labels in response to the pH modulation, which may be detected by a fluorescence microscope known in the art. In particular embodiments, the optical signal may also refer to the difference between the detected optical output (e.g. fluorescence intensities) at various stages of the present method. For example, the optical signal may refer to the change in fluorescence intensity detected before and after a potential or current is applied to the electrode as disclosed herein.

The pH modulation of the present method may be carried out by applying current or voltage to the electrode. In some embodiments, the electric potential or current used herein for pH modulation may be defined by a waveform capable of being modulated based on open-loop and/or closed-loop control scheme to change the size of the pH modulated zone. For example, the size of the pH modulated zone adjacent to the surface of the electrode or the coating on the electrode may be controlled by adjusting the parameters of the waveform. In certain embodiments, the height of the zone (z height) may be changed causing a change in the number of activated pH-sensitive labels on the biospecimen, and the resulting change in optical signal (e.g., fluorescence) may be analyzed over the duration of the imaging process (time analysis). For example, a measurement of activated fluorophores on the biospecimen for a zone height up to about 300 nm from the electrode surface may be made, followed by repeating such measurement of activated fluorophores for a zone height up to about 350 nm. From these results, the signal contribution from a 50 nm portion (difference between the two measurements) can be resolved.

In some embodiments, the surface of the electrode or the coating on the surface of the electrode includes microstructures to which the biospecimen may be coupled (e.g., by adherence, chemical bonding, or other interactions), defining a volume between the biospecimen and surface (e.g. between the biospecimen and the microstructures on the surface or the coating), through which the pH modulating agent diffuses. For example, a pH modulating agent dissolved in the buffered solution may diffuse through this volume.

In certain embodiments, the coupling (e.g., adherence, chemical bonding, or other interactions) of the biospecimen to the surface or the coating with the microstructures is at a higher degree than the coupling of the biospecimen to the surface or the coating without the microstructures. For example, the microstructure may promote adhesion or binding of the biospecimen (such as a cell) to the surface of the electrode. In certain embodiments, the microstructures may also provide an additional way to change the actual imaging area of the biospecimen. For the same height of the pH modulation zone, the area (or amount) of the activated fluorophores on the biospecimen may be different depending on the height of the microstructures where the biospecimen is coupled. For example, if the pH modulation zone has a zone height up to about 500 nm and the height of the microstructures is 450 nm, the actual signal contributed from the biospecimen may be 50 nm. If the height of the microstructures is 400 nm, the signal contribution may be from 100 nm of the biospecimen.

In certain embodiments, the concentration of the pH modulating agent in the volume between the biospecimen and the surface with the microstructures is higher than the concentration of the pH modulating agent in the volume between the biospecimen and the surface of the electrode or the coating without the microstructures. For example, upon coupling the biospecimen (such as a cell) to the electrode surface or the coating then upon activation, there may be a localized depletion of the pH modulating agent as the biospecimen blocks diffusion of the buffered solution to bring new redox molecules to modulate the pH. The microstructuring may increase the size of the pH zone generated between the biospecimen and the electrode surface. By having a microstrucutred electrode surface, the extent of depletion is reduced as there is more volume between the biospecimen and the electrode surface to supply the pH modulating agent, therefore maintaining the pH modulated zone. Thus, the microstructures may enable sufficient availability of the pH modulating agent to change the pH of a zone adjacent to the surface of the electrode Suitable electrical control units include, but are not limited to, electronics that have current/voltage source output and sense input, software that controls electrical parameters.

The electrode may be included in a substrate, such as a glass substrate, on which the imaging of the biospecimen may be performed. Suitable substrates include those with patterned electrodes, including working electrode (WE) and/or sensing electrode (SE). At least one electrode (WE) is used in the disclosed method. A sensing electrode may be optionally used in the disclosed method.

Counter electrode (CE) and reference electrode (RE) are generally used in the present methods for electrochemical control. These electrodes may be external electrodes or electrodes incorporated to the substrate.

In some embodiments, the present method may include a closed-loop control unit. Monitoring actual pH during the modulation via pH sensing electrode signal may allow implementation of a closed-loop control, which enables faster and more precise pH control. Examples of suitable closed-loop control units for controlling pH close to electrode surface include, but are not limited to, those described in US20170010238, which is incorporated herein by reference in its entirety.

In some embodiments, the substrate is a glass slide. Example of glass slide substrate, electrodes, and control units include those described in U.S. Pat. No. 9,910,008, which is incorporated herein by reference in its entirety.

In some embodiments, the present method further comprises conducting imaging the biospecimen in an array of controlling and/or imaging modules, each module comprising an independent cycle of (a)-(d) as disclosed herein. Suitable array technologies include, but are not limited to, complementary metal-oxide semiconductor (CMOS) array, electrode array, thin-film transistor (TFT) array, and others known in the art. Examples of suitable arrays include the multisite arrays as described in U.S. Pat. No. 9,810,688, the entire contents of which are incorporated herein by reference.

Representative Imaging Process

Figure 1B:
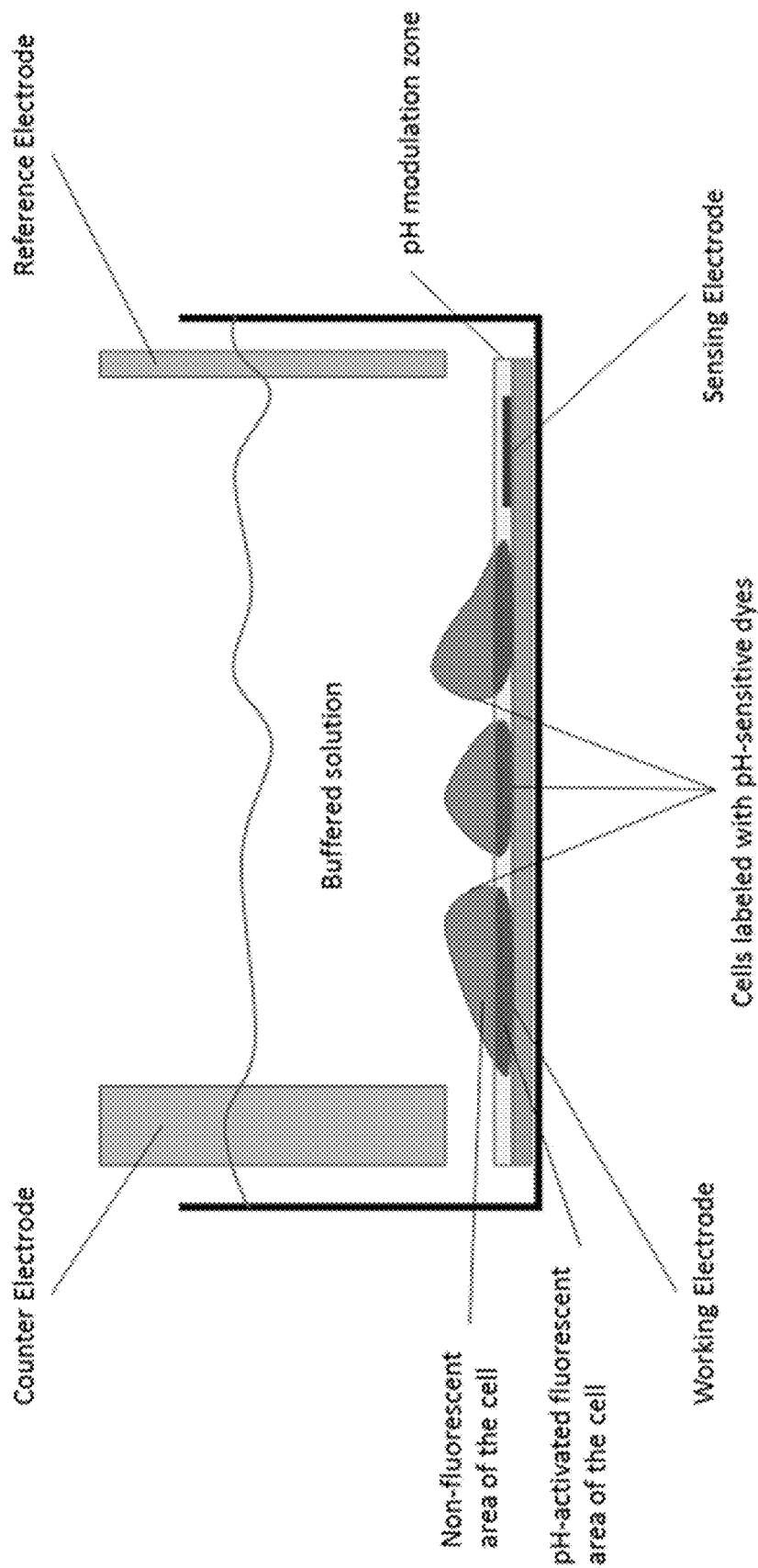
FIG. 1B is a schematic illustrating a system for pH-modulated imaging, in which pH modification is in effect.

A schematic illustration of the present method is shown in FIGS. 1A and 1B. Instead of using a special optical or physical setting, simple electrical control unit with electrode-patterned substrate is utilized. When pH modulation is not in effect (FIG. 1A), the pH-sensitive dyes on the biospecimen (e.g., cell) is not activated, and no optical signal is observed. When a potential is applied to the working electrode (FIG. 1B), a pH modulation zone is created adjacent to the surface of the electrode, thereby activating the pH-sensitive dyes within the zone to produce an optical signal (e.g., fluorescence).

Figure 2:
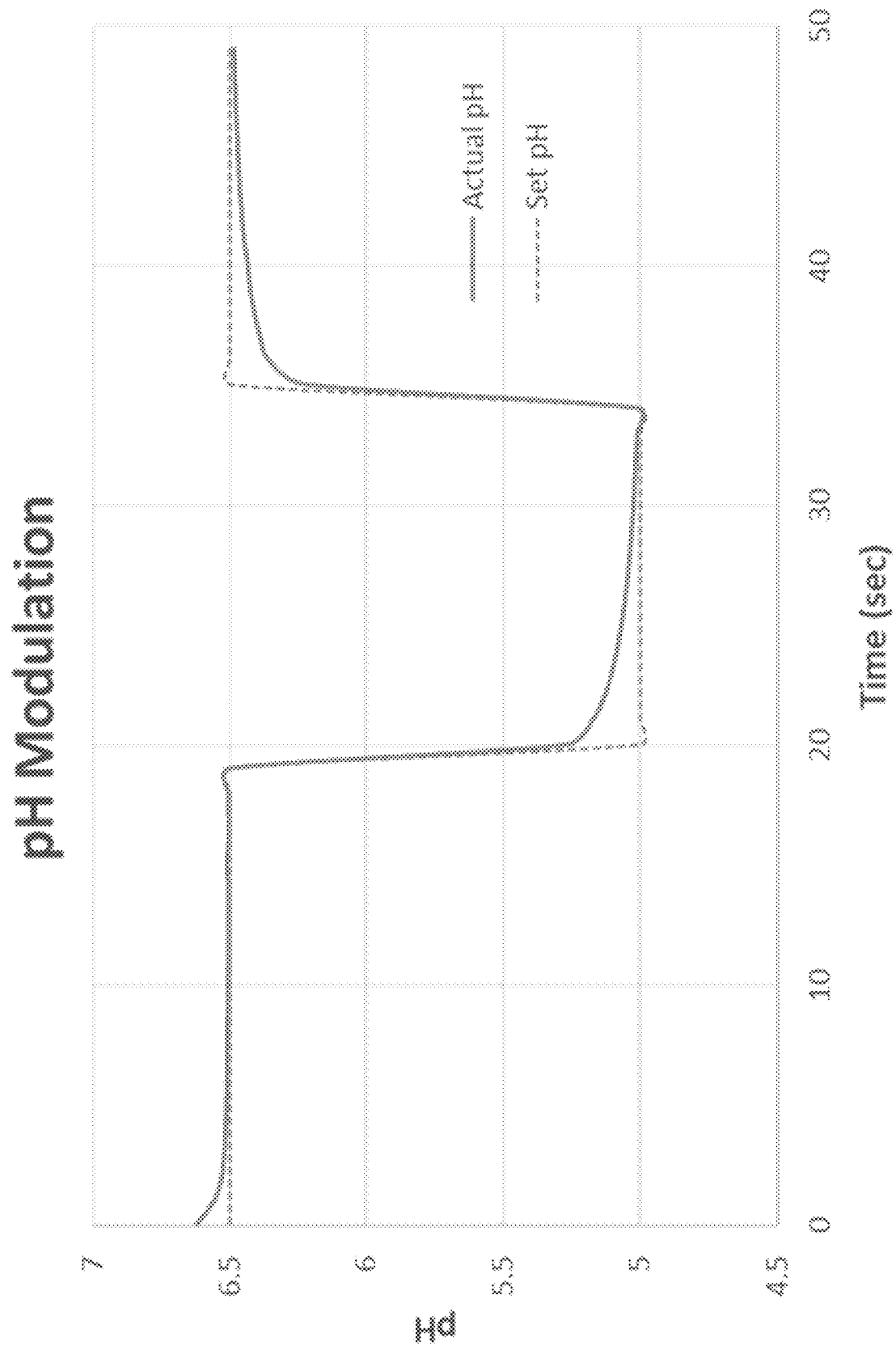
FIG. 2 is a graph showing the changing pH of a solution via oxidation/reduction of quinones in 1 mM phosphate buffer on an indium tin oxide electrode. The pH values were determined by a pre-calibrated iridium oxide sensing electrode patterned on the surface and the closed-loop control achieved the target pH values in an accurate and rapid manner.

Reversible electrochemical oxidation/reduction of pH modulating agents such as quinone derivatives, hydrazine derivatives, or water can induce rapid pH change in a local region. It has been demonstrated that pH can be modulated with quinone derivative in the range of 3 to 10. The pH modulation limit may depend on the pKa and oxidation/reduction potential of the specific pH modulating agents and their concentration. FIG. 2 shows the on-demand pH modulation by the oxidation of 2,5-dimethylhydroquinone on indium-tin oxide electrode in 1 mM phosphate buffer. When anodic current is applied to the electrode, the proton production overcomes the buffer capacity and pH of the solution becomes more acidic. This is an example for the use case of selectively imaging a pH sensitive dye that has an optimal fluorescence at acidic pH such as pHrodo or Protonex.

In case where pH modulating agents are immobilized to the coating layer, the amount of pH modulating agents may be a limiting factor and it may introduce a time duration limit—between 1 µs and 1 min. In this case, a pulse-based modulation scheme may be more appropriate. A single voltage or current pulse may generate a pH modulation window that may last temporarily, which may allow single-time imaging with a short time duration. If the redox process of the selected pH modulating agents is reversible, which is the case of quinones for example, performing multiple rounds of imaging may be possible through the oxidation/reduction cycles.

The thickness of the pH modulation zone may be controlled by adjusting the buffering capacity of the solution and electrical control parameters. A higher buffer capacity will result in a thinner modulation zone, as would the current ramp associated with the electrical pulse or the time allowed between the start of the pulse and the start of the image collection, among other factors. In this way, pH-modulated imaging may allow any existing fluorescence microscope to produce images similar to TIRF microscopy or confocal microscopy focused on the volume very close to the substrate. In principle, pH-modulated imaging may be used in conjunction with any of these techniques to further improve the image capability by adding dynamic control of the imaging environment through pH control.

Figure 3A:
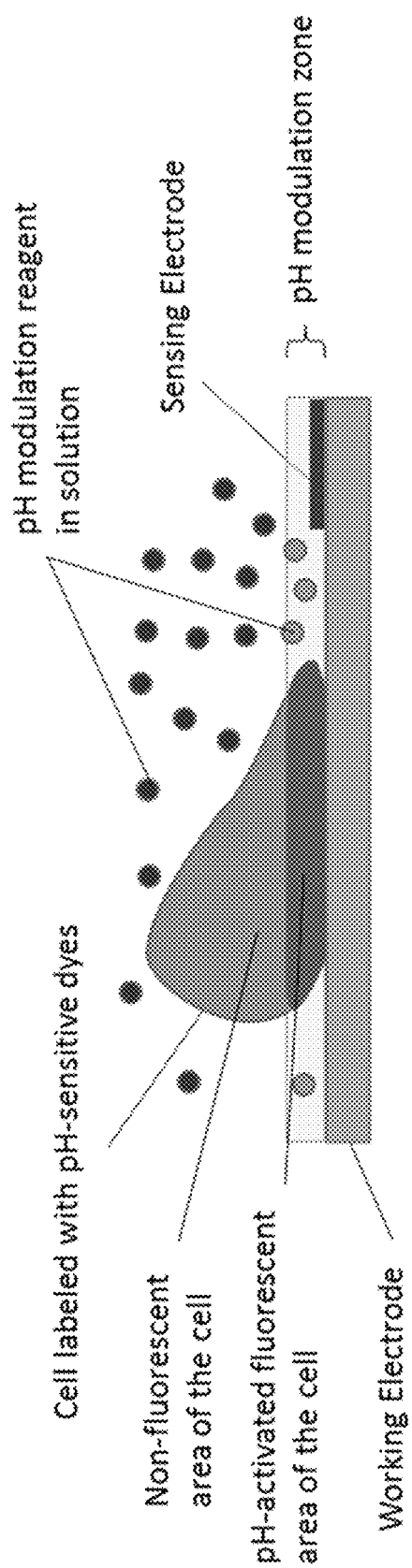
FIG. 3A is a schematic illustrating an exemplary configuration of a pH-modulated imaging substrate, in which a pH modulating agent is in solution

FIGS. 3A-3D show exemplary configurations of the different experimental schemes. FIG. 3A shows the case where pH modulating agent is added to the solution. In this case, continuous pH modulation for a longer time duration may be carried out. For live-cell imaging, however, biocompatible pH modulating agents, which do not interfere with cells' physiological functions, may be used.

Figure 3B:
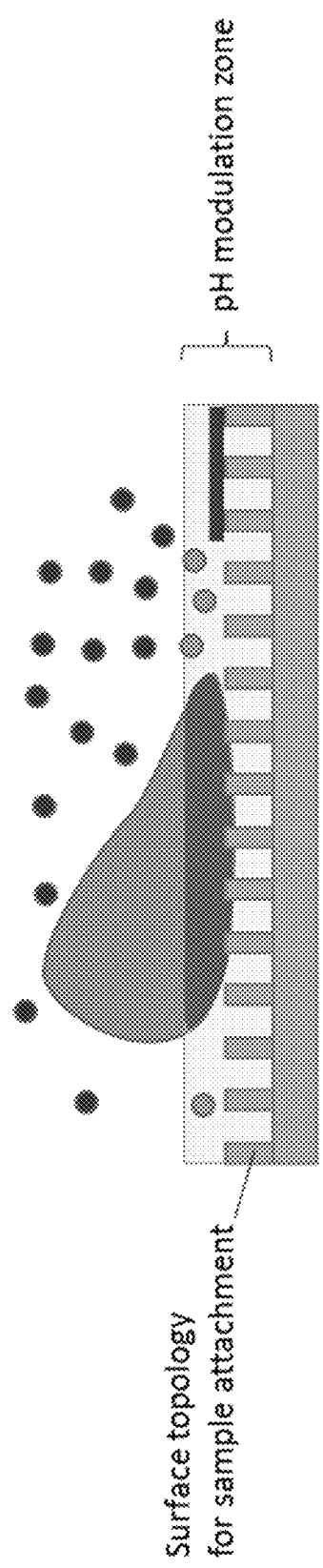
FIG. 3B is a schematic illustrating an exemplary configuration of a pH-modulated imaging substrate similar to FIG. 3A with additional surface topological structures.
Figure 3C:
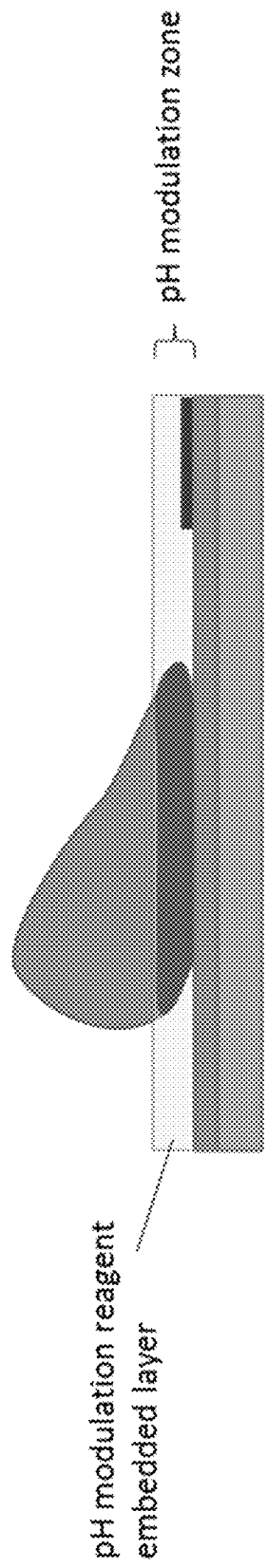
FIG. 3C is a schematic illustrating an exemplary configuration of a pH-modulated imaging substrate, in which a pH modulating agent is embedded in a coating layer.

FIG. 3C shows the case of using a coating layer that has embedded pH modulating agents. In this scenario, direct contact between pH modulating agents and target biospecimen may be minimized (as compared to having the pH modulating agent dissolved throughout the buffered solution) and the adverse effects of pH modulating agents, if any, may be decreased.

Figure 3D:
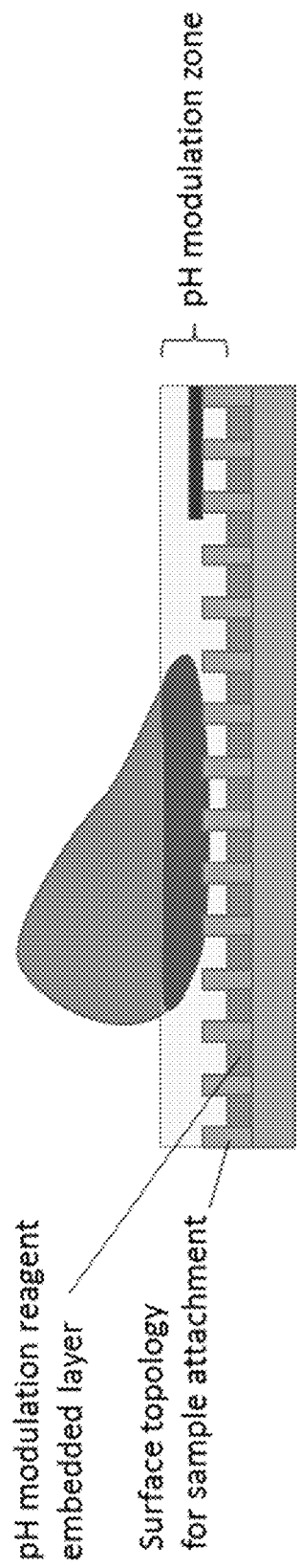
FIG. 3D is a schematic illustrating an exemplary configuration of a pH-modulated imaging substrate similar to FIG. 3C with additional surface topological structures.

As shown in FIG. 3B and FIG. 3D, the substrate may have additional topological structures (e.g., microstructures) through nano- and/or micro-fabrication or surface chemistry, etc. These features may introduce a stronger adhesion of biospecimen to the electrode substrate, act as an additional signaling cue for cellular biology, and serve another source of controlling 3D structural variation.

The pH modulation may be based on diffusion, and the timing for the imaging and specific combination of electrical parameters may be used to control the height above the electrode that the image is captured from. By taking multiple images over a time period, a 3-D model of the objects near the electrode surface may be generated. In some embodiments, a pulse-type stimulation may be used, and multiple pH modulation pulses may be applied to obtain a set of images that are taken over time for a long-term time-lapse monitoring.

Advantages

The present method involves the use of electrochemical pH modulation in combination with pH-sensitive dyes to achieve localized imaging of biospecimen such as tissue samples, cells and small vesicles with a high vertical axial resolution, similar to confocal microscopy or total internal reflectance fluorescence (TIRF) microscopy. The pH modulating agents, either in solution or in a thin layer on the surface of electrodes, may be electrochemically oxidized or reduced to generate a pH modulation zone covering a nano- to micro-meter distance from the surface. In particular embodiments, fluorescence from pH-sensitive dyes within the pH modulation zone that contains a part of the imaging object may contribute to the signal. Thus, the present method may be employed to temporarily visualize only a thin slice of the sample close to the electrode surface by taking images during the active pH modulation period.

The present method may enable performance of surface-focused imaging with a regular fluorescent microscope by simply utilizing an electrochemical pH modulation unit and slides. In addition, the imaging window size may be controlled by non-optical parameters such as electrical inputs, microstructure, pH modulating agent concentration and buffer concentration, etc. Further, pH modulation may provide additional control over biochemical interactions. For example, some enzymes have pH-dependence in their activities; protecting groups of a functional group in a molecule may be also controlled by pH; specificity, sensitivity, and reproducibility of antibody-based detection in serum may be improved by performing the test in various pH conditions, which can be extended to immunostaining applications.

In some embodiments, biocompatible pH modulating agents may be employed, such as those suitable for a live cell imaging. The biocompatible pH modulating agents may include chemical modification and/or may be immobilized on the electrode, which may minimize the direct interaction of such agents with the biospecimen being imaged.

Various features, advantages, and embodiments are set forth in the following claims.

What is claimed is:

1. A method for imaging a biospecimen, comprising
   (a) labeling the biospecimen with a pH-sensitive label to form a labeled biospecimen,
   (b) submerging the labeled biospecimen and a surface of an electrode in a buffered solution having a pH value, wherein
      the buffered solution comprises a pH modulating agent;
      the surface optionally comprises microstructures;
      the labeled biospecimen is coupled to the surface or to the microstructures; and
      the microstructures, when present, define a volume between the biospecimen and the surface, through which the pH modulating agent diffuses,
   (c) applying a potential or a current to the electrode, whereupon the pH modulating agent causes a change in the pH value in a zone adjacent to the surface of the electrode, thereby causing the pH-sensitive label within the zone to produce an optical signal, and
   (d) detecting the optical signal thereby imaging the labeled biospecimen,
   wherein the biospecimen is a fixed tissue, a cell, a vesicle, or a combination thereof.

2. The method of claim 1, wherein the pH modulating agent is a quinone derivative, an aminophenol derivative, an aniline derivative, a benzidine derivative, a hydrazine derivative, phenol-Ru(2,2'-bipyridine)$_3^{2+}$, or a combination thereof.

3. The method of claim 2, wherein the pH modulating agent is any of formula (I)-(XII)

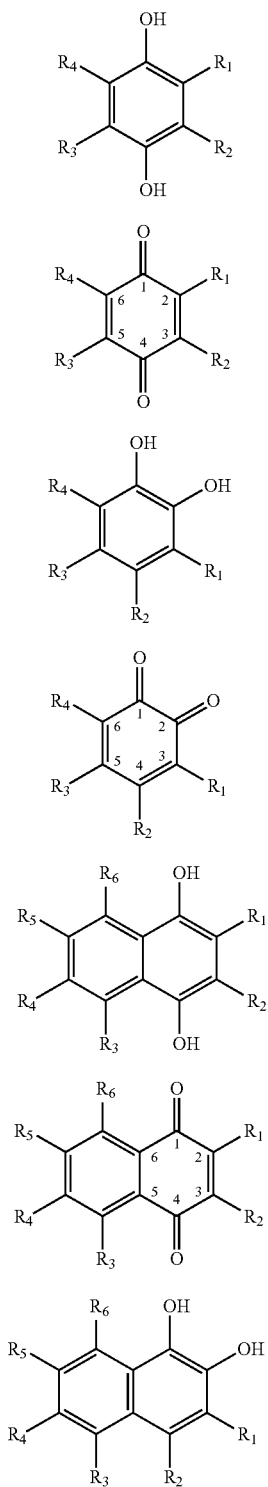

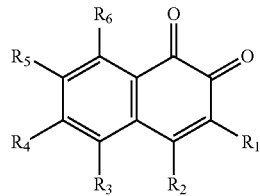

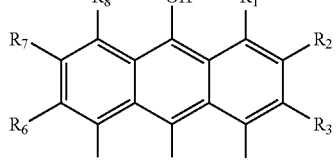

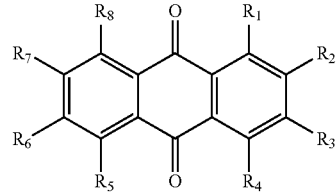

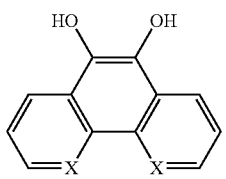

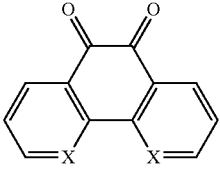

wherein $R_1$, $R_2$, $R_3$, $R_4$, $R_5$, $R_6$, $R_7$, and $R_8$ are each independently selected from the group consisting of: H; $C_nH_{2n+1}$; Cl; F; I, Br, OM, NO$_2$, OH, OC$_n$H$_{2n}$, OC$_n$H$_{2n}$OH, O(C$_n$H$_{2n}$O)$_y$OH, O(C$_n$H$_{2n}$O)$_y$OC$_n$H$_{2n+1}$, O(C$_n$H$_{2n}$O)$_y$COOH; O(C$_n$H$_{2n}$O)$_y$COOM; COOH; COOM; COOC$_n$H$_{2n+1}$; CONHC$_n$H$_{2n+1}$; CON(C$_n$H$_{2n+1}$)$_2$; SO$_3$H; SO$_3$M; NH$_2$; NHC$_n$H$_{2n+1}$; N(C$_n$H$_{2n+1}$)$_2$; NHC$_n$H$_{2n}$OH; NHC$_n$H$_{2n}$NH$_2$; N(C$_n$H$_{2n}$OH)$_2$; N(C$_n$H$_{2n}$NH)$_2$; NHCOC$_n$H$_{2n+1}$; NC$_n$H$_{2n}$COC$_n$H$_{2n+1}$; NC$_n$H$_{2n}$COC$_n$H$_{2n}$OH; NC$_n$H$_{2n}$COC$_n$H$_{2n}$NH$_2$; NC$_n$H$_{2n}$COC$_n$H$_{2n}$SH; SH; SC$_n$H$_{2n+1}$; SC$_n$H$_{2n}$OH; S(C$_n$H$_{2n}$O)$_y$OH; S(C$_n$H$_{2n}$O)$_y$OC$_n$H$_{2n+1}$; S(C$_n$H$_{2n}$O)$_y$COOH; S(C$_n$H$_{2n}$O)$_y$COOM; OC$_n$H$_{2n}$SH; O(C$_n$H$_{2n}$O)$_y$SH; O(C$_n$H$_{2n}$O)$_y$SC$_n$H$_{2n+1}$; C$_n$H$_{2n}$; C$_n$H$_{2n}$OC$_n$H$_{2n}$; C$_n$H$_{2n}$SC$_n$H$_{2n}$; C$_n$H$_{2n}$NHC$_n$H$_{2n}$; C$_n$H$_{2n}$N(C$_n$H$_{2n+1}$) C$_n$H$_{2n}$; C$_n$H$_{2n+1}$; C$_n$H$_{2n}$OH; C$_n$H$_{2n+1}$OC$_n$H$_{2n}$; C$_n$H$_{2n}$OC$_n$H$_{2n}$OH; C$_n$H$_{2n}$O(C$_n$H$_{2n}$O)$_y$COOH; C$_n$H$_{2n}$O(C$_n$H$_{2n}$O)$_y$COOM; C$_n$H$_{2n}$COOH; C$_n$H$_{2n}$COOM; C$_n$H$_{2n}$COOC$_n$H$_{2n+1}$; C$_n$H$_{2n}$CONHC$_n$H$_{2n+1}$; C$_n$H$_{2n}$CONH(C$_n$H$_{2n+1}$)$_2$; C$_n$H$_{2n}$SO$_3$H; C$_n$H$_{2n}$SO$_3$M; C$_n$H$_{2n}$NH$_2$; C$_n$H$_{2n}$NHC$_n$H$_{2n+1}$; C$_n$H$_{2n}$N(C$_n$H$_{2n+1}$)$_2$; C$_n$H$_{2n}$NHC$_n$H$_{2n}$OH; C$_n$H$_{2n}$NHC$_n$H$_{2n}$NH$_2$; C$_n$H$_{2n}$N $(C_nH_{2n}OH)_2$; $C_nH_{2n}N(C_nH_{2n}NH_2)_2$; $C_nH_{2n}NHCOC_nH_{2n+1}$; $C_nH_{2n}NC_nH_{2n}COC_nH_{2n}OH$; $C_nH_{2n}NC_nH_{2n}COC_nH_{2n}NH_2$; $C_nH_{2n}NC_nH_{2n}COC_nH_{2n}SH$; $C_nH_{2n}SH$; $C_nH_{2n+1}SC_nH_{2n}$; $C_nH_{2n}SC_nH_{2n}OH$; $C_nH_{2n}S(C_nH_{2n}O)_yOH$; $C_nH_{2n}S(C_nH_{2n}O)_yOC_nH_{2n+1}$; $C_nH_{2n}S(C_nH_{2n}O)_yCOOH$; $C_nH_{2n}S(C_nH_{2n}O)_yCOOM$; sugars; peptides; and amino acids, wherein M is any metal cation or $NH_4^+$, n is an integer from 1 to $10^9$, and y is an integer from 1 to $10^9$.

4. The method of claim 1, wherein the pH sensitive label is a fluorescent dye, a fluorescent protein, an enzyme, or a combination thereof.

5. The method of claim 4, wherein the pH sensitive label is fluorescein, a fluorescein amidite, a rhodamine B derivative, a horseradish peroxidase, a glucose oxidase, or an alkaline phosphatase.

6. The method of claim 1, wherein the optical signal is colorimetric signal, a chemiluminescent signal, or a fluorescent signal.

7. The method of claim 1, wherein the potential in (c) is defined by a waveform capable of being modulated based on open-loop and/or closed-loop control scheme to change the size of the zone adjacent to the surface of the electrode.

8. The method of claim 1, wherein the coupling between the biospecimen to the microstructures in (b) is at a higher degree than the coupling of the biospecimen to the surface without the microstructure, or wherein the concentration of the pH modulating agent in the volume between the biospecimen and the surface with the microstructures is higher than the concentration of the pH modulating agent in the volume between the biospecimen and the surface without the microstructure.

9. The method of claim 1, further comprising conducting imaging the biospecimen in an array of controlling and/or imaging modules, each module comprising an independent cycle of performing (a)-(d), wherein the array of controlling and/or imaging modules is a complementary metal-oxide semiconductor (CMOS) array, an electrode array, or a thin-film transistor (TFT) array.

10. The method of claim 1, wherein the biospecimen is a fixed tissue.

11. A method for imaging a biospecimen, comprising
(a) labeling the biospecimen with a pH-sensitive label to form a labeled biospecimen,
(b) submerging the labeled biospecimen and a surface of an electrode in a buffered solution having a pH value, wherein
the surface comprises a coating;
the coating comprises a pH modulating agent;
the coating optionally comprises microstructures;
the buffered solution optionally comprises the pH modulating agent;
the labeled biospecimen is coupled to the coating or to the microstructures; and
the microstructures, when present, define a volume between the biospecimen and the surface, through which the pH modulating agent in the buffered solution, when present, diffuses,
(c) applying a potential or a current to the electrode, whereupon the pH modulating agent causes a change in the pH value in a zone adjacent to the coating, thereby causing the pH-sensitive label within the zone to produce an optical signal, and
(d) detecting the optical signal thereby imaging the labeled biospecimen,
wherein the biospecimen is a fixed tissue, a cell, a vesicle, or a combination thereof.

12. The method of claim 11, wherein the pH modulating agent is a quinone derivative, an aminophenol derivative, an aniline derivative, a benzidine derivative, a hydrazine derivative, phenol-Ru(2,2'-bipyridine)$_3^{2+}$, or a combination thereof.

13. The method of claim 12, wherein the pH modulating agent is any of formula (I)-(XII)

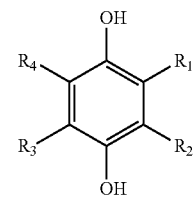

(I)

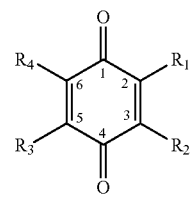

(II)

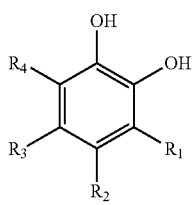

(III)

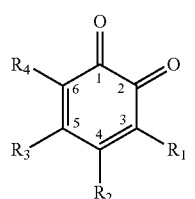

(IV)

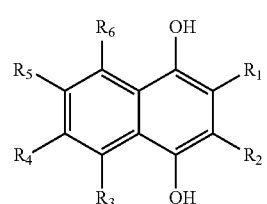

(V)

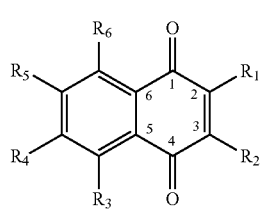

(VI)

-continued

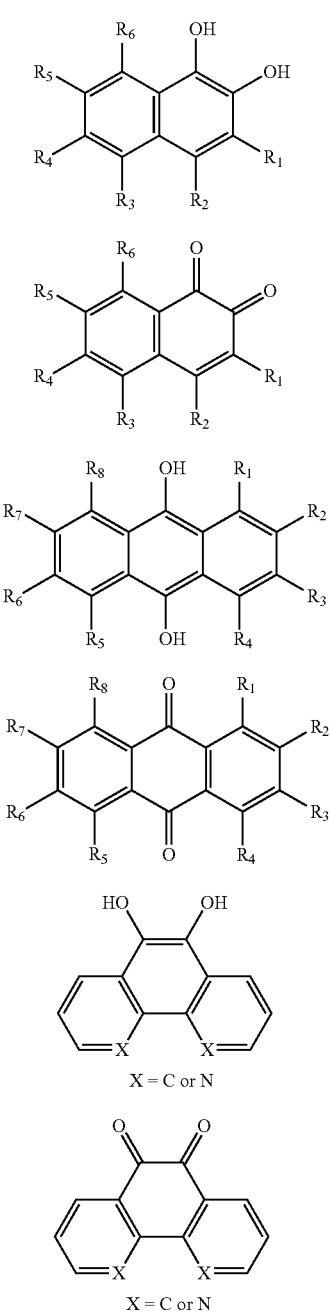

wherein $R_1$, $R_2$, $R_3$, $R_4$, $R_5$, $R_6$, $R_7$, and $R_8$ are each independently selected from the group consisting of: H; $C_nH_{2n+1}$; Cl; F; I, Br, OM, $NO_2$, OH, $OC_nH_{2n}$, $OC_nH_{2n}OH$, $O(C_nH_{2n}O)_yOH$, $O(C_nH_{2n}O)_yOC_nH_{2n+1}$, $O(C_nH_{2n}O)_yCOOH$; $O(C_nH_{2n}O)_yCOOM$; COOH; COOM; $COOC_nH_{2n+1}$; $CONHC_nH_{2n+1}$; $CON(C_nH_{2n+1})_2$; $SO_3H$; $SO_3M$; $NH_2$; $NHC_nH_{2n+1}$; $N(C_nH_{2n+1})_2$; $NHC_nH_{2n}OH$; $NHC_nH_{2n}NH_2$; $N(C_nH_{2n}OH)_2$; $N(C_nH_{2n}NH)_2$; $NHCOC_nH_{2n+1}$; $NC_nH_{2n}COC_nH_{2n+1}$; $NC_nH_{2n}COC_nH_{2n}OH$; $NC_nH_{2n}COC_nH_{2n}NH_2$; $NC_nH_{2n}COC_nH_{2n}SH$; SH; $SC_nH_{2n+1}$; $SC_nH_{2n}OH$; $S(C_nH_{2n}O)_yOH$; $S(C_nH_{2n}O)_yOC_nH_{2n+1}$; $S(C_nH_{2n}O)_yCOOH$; $S(C_nH_{2n}O)_yCOOM$; $OC_nH_{2n}SH$; $O(C_nH_{2n}O)_ySH$; $O(C_nH_{2n}O)_ySC_nH_{2n+1}$; $C_nH_{2n}$; $C_nH_{2n}OC_nH_{2n}$; $C_nH_{2n}SC_nH_{2n}$; $C_nH_{2n}NHC_nH_{2n}$; $C_nH_{2n}N(C_nH_{2n+1})C_nH_{2n}$; $C_nH_{2n+1}$; $C_nH_{2n}OH$; $C_nH_{2n+1}OC_nH_{2n}$; $C_nH_{2n}OC_nH_{2n}OH$; $C_nH_{2n}O(C_nH_{2n}O)_yCOOH$; $C_nH_{2n}O(C_nH_{2n}O)_yCOOM$; $C_nH_{2n}COOH$; $C_nH_{2n}COOM$; $C_nH_{2n}COOC_nH_{2n+1}$; $C_nH_{2n}CONHC_nH_{2n+1}$; $C_nH_{2n}CONH(C_nH_{2n+1})_2$; $C_nH_{2n}SO_3H$; $C_nH_{2n}SO_3M$; $C_nH_{2n}NH_2$; $C_nH_{2n}NHC_nH_{2n+1}$; $C_nH_{2n}N(C_nH_{2n+1})_2$; $C_nH_{2n}NHC_nH_{2n}OH$; $C_nH_{2n}NHC_nH_{2n}NH_2$; $C_nH_{2n}N(C_nH_{2n}OH)_2$; $C_nH_{2n}N(C_nH_{2n}NH_2)_2$; $C_nH_{2n}NHCOC_nH_{2n+1}$; $C_nH_{2n}NC_nH_{2n}COC_nH_{2n}OH$; $C_nH_{2n}NC_nH_{2n}COC_nH_{2n}NH_2$; $C_nH_{2n}NC_nH_{2n}COC_nH_{2n}SH$; $C_nH_{2n}SH$; $C_nH_{2n+1}SC_nH_{2n}$; $C_nH_{2n}SC_nH_{2n}OH$; $C_nH_{2n}S(C_nH_{2n}O)_yOH$; $C_nH_{2n}S(C_nH_{2n}O)_yOC_nH_{2n+1}$; $C_nH_{2n}S(C_nH_{2n}O)_yCOOH$; $C_nH_{2n}S(C_nH_{2n}O)_yCOOM$; sugars; peptides; and amino acids, wherein M is any metal cation or $NH_4^+$, n is an integer from 1 to $10^9$, and y is an integer from 1 to $10^9$.

14. The method of claim 11, wherein the pH sensitive label is a fluorescent dye, a fluorescent protein, an enzyme, or a combination thereof.

15. The method of claim 14, wherein the pH sensitive label is fluorescein, a fluorescein amidite, a rhodamine B derivative, a horseradish peroxidase, a glucose oxidase, or an alkaline phosphatase.

16. The method of claim 11, wherein the coating comprises a polymer and the pH modulating agent is integrated in the polymer as a part of a backbone of the polymer or as a side chain of the polymer.

17. The method of claim 11, wherein the potential in (c) is defined by a waveform capable of being modulated based on open-loop and/or closed-loop control scheme to change the size of the zone adjacent to the coating.

18. The method of claim 11, wherein the coupling of the biospecimen to the coating with the microstructure in (b) is at a higher degree than the coupling of the biospecimen to the coating without the microstructure, or wherein the concentration of the pH modulating agent in the volume between the biospecimen and the surface with the microstructures is higher than the concentration of the pH modulating agent in the volume between the biospecimen and the surface without the microstructure.

19. The method of claim 11, further comprising conducting imaging the biospecimen in an array of controlling and/or imaging modules, each module comprising an independent cycle of performing (a)-(d), wherein the array of controlling and/or imaging modules is a complementary metal-oxide semiconductor (CMOS) array, an electrode array, or a thin-film transistor (TFT) array.

20. The method of claim 11, wherein the biospecimen is a fixed tissue.

* * * * *